United States Patent [19]

Roteman

[11] 4,251,532
[45] Feb. 17, 1981

[54] 1-(4-AMINO-6,7-DIMETHOXY-2-QUINAZOLINYL)-4-(2-TETRAHYDROFUROYL)PIPERAZINE HYDROCHLORIDE DIHYDRATE

[75] Inventor: Robert Roteman, Waukegan, Ill.

[73] Assignee: Abbott Laboratories, North Chicago, Ill.

[21] Appl. No.: 78,317

[22] Filed: Sep. 24, 1979

Related U.S. Application Data

[63] Continuation-in-part of Ser. No. 904,667, May 10, 1978, abandoned, which is a continuation of Ser. No. 821,675, Aug. 4, 1977, abandoned.

[51] Int. Cl.$^3$ .................. A61N 31/505; C07D 405/14
[52] U.S. Cl. ..................................... 424/251; 544/291
[58] Field of Search ......................... 544/291; 424/251

[56] References Cited

U.S. PATENT DOCUMENTS

| 4,026,894 | 5/1977 | Winn et al. | 544/291 |
| 4,092,315 | 5/1978 | Bianco | 544/291 |

Primary Examiner—Paul M. Coughlan, Jr.
Attorney, Agent, or Firm—Robert L. Niblack

[57] ABSTRACT

An improved anti-hypertensive agent, the hydrochloride salt of 1-(4-amino-6,7-dimethoxy-2-quinazolinyl)-4-(2-tetrahydrofuroyl)piperazine dihydrate.

3 Claims, 2 Drawing Figures

1-(4-AMINO-6,7-DIMETHOXY-2-QUINAZOLINYL)-4-(2-TETRAHYDROFUROYL)-PIPERAZINE HYDROCHLORIDE DIHYDRATE

CROSS-REFERENCE TO RELATED APPLICATIONS

This application is a continuation-in-part of commonly assigned, co-pending application Ser. No. 904,667, filed May 10, 1978, now abandoned which is a continuation of application Ser. No. 821,675, filed Aug. 4, 1977, now abandoned.

BACKGROUND OF THE INVENTION

In recent years there has been an increased recognition of the seriousness of uncontrolled hypertension. The disease is particularly dangerous because it is, in most instances silent, and can result in stroke or heart attack if left untreated for a period of time. Because the etiology of most cases of hypertension is not understood, the search for effective anti-hypertensive agents has been largely empirical. This approach has led to a number of useful drugs with widely varied mechanisms of action.

One such drug has been recently introduced to the market and represents the first in a new chemical class of antihypertensive agents, the hydrochloride salt of 1-(4-amino-6,7-dimethoxy-2-quinazolinyl-4-(2-furanyl-carbonyl)piperazine, which has the generic name prazosin hydrochloride. Prazosin hydrochloride is represented by the formula:

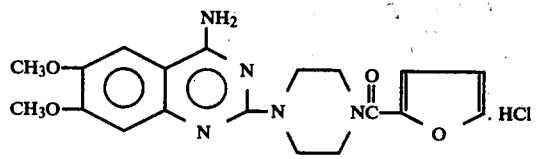

This drug however, as reported in The Lancet, May 10, 1975, at page 1095, exhibits significant toxicity and can cause a profound fall in blood pressure. Sudden collapse with loss of consciousness for periods ranging from a few minutes to one hour following use of this drug have been reported. (The Lancet and British Medical Journal, June 28, 1975, pages 727, 728. See also *The Physicians Desk Reference*, 33rd Edition, p. 1343, Medical Economics Co. (1979). Furthermore, the compound is relatively insoluble in water and is not administered parenterally.

A related compound, the hydrochloride salt of 1-(4-amino-6,7-dimethoxy-2-quinazolinyl)-4-(2-tetrahydrofuroyl) piperazine has also been reported to be useful as an antihypertensive agent, is less toxic than prazosin hydrochloride, is highly soluble in water and can be administered parenterally as well as orally. See U.S. Pat. No. 4,026,894 (The compound is named 2[4(tetrahydro-2-furoyl)-piperazino]-4-amino-6,7-dimethoxyquinazoline therein). The newly reported compound, hereinafter referred to as the compound of Formula II, is represented by the formula:

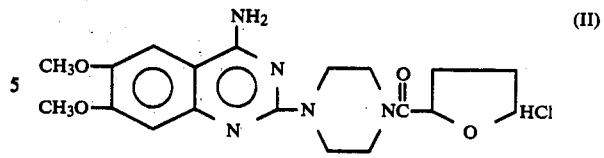

The compound of Formula II, because of its greatly enhanced solubility, can be administered parenterally, whereas prazosin hydrochloride is only available in tablet form for oral administration. Thus prazosin cannot be used in emergency situations which require intravenous administration of an effective antihypertensive agent to rapidly lower blood pressure in a patient suffering from a hypertensive crisis.

It has now surprisingly been found that the dihydrate of the compound of Formula II has numerous advantages over the anhydrous compound. The dihydrate, while less water soluble than the compound of Formula II, is far more stable in solution that the compound of Formula II and thus is considerably more suitable for parenteral administration. Furthermore, the compound of this invention is more stable when stored in bulk prior to tableting than the compound of Formula II which is hygroscopic and thus picks up moisture upon storage. The lessened tendency toward hygroscopicity of the compound of this invention is very important because the accuracy of weighing out bulk compound for tableting purposes would be affected if the compound's weight is partially attributable to water of hydration. Thus, constant assaying would be required to ensure that the proper amount of active drug is provided. Tableting accuracy is particularly critical since the drug is effective at such small dosages.

While the compound of Formula II is highly useful as an anti-hypertensive agent, the compound of this invention has the added advantages of ease of manufacture, stability in solution, lends itself to more accurate tableting procedures and is far less hydroscopic which results in greater physical stability and greater ease of assaying drug content.

SUMMARY OF THE INVENTION

This invention relates to an improved anti-hypertensive agent, the hydrochloride salt of 1-(4-amino-6,7-dimethoxy-2-quinazolinyl)-4-(2-tetrahydrofuroyl)piperazine dihydrate. The compound is represented by the Formula III:

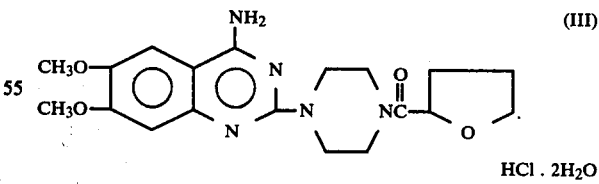

The compound of this invention is useful as an antihypertensive agent, and can be administered either orally or parenterally.

DETAILED DESCRIPTION OF THE PREFERRED EMBODIMENTS

Figure 1:
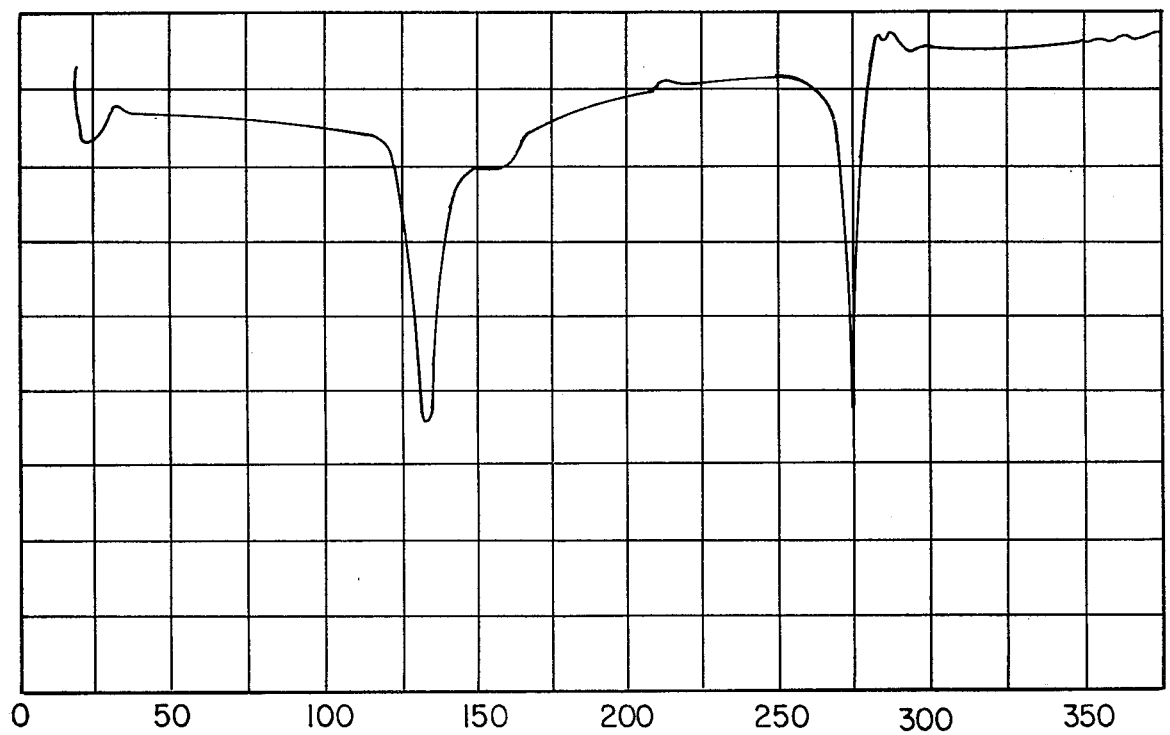

The compound of this invention, 1-(4-amino-6,7-dimethoxy-2-quinazolinyl)-4-(2-tetrahydrofuroyl)piperazine hydrochloride dihydrate, represented by Formula III supra, is useful as an anti-hypertensive agent. The compound is effective at daily dosages of from 0.01 to 100 milligrams, and preferably is administered orally in divided disages. In the event of a hypertensive crisis, the compound is administered by the intravenous route.

Generally speaking, the compound of this invention is prepared by slurrying or suspending the base, 1-(4-amino-6,7-dimethoxy-2-quinazolinyl)-4-(2-tetrahydrofuroyl)piperazine with concentrated aqueous hydrochloric acid, in, for example, 190 proof 3A alcohol, heating the mixture to about 35° to 40° C. adding concentrated aqueous hydrochloric acid to the slurry and thereafter heating the mixture to a temperature of between about 70° to 75° C. The reaction mixture can then be treated with carbon and the carbon filtered off, however carbon treatment is optional. If carbon is not used, the mixture is filtered, the filtrate is chilled and the compound of this invention is filtered off and dried in vacuo or air dried at a temperature of about 60° C.

The base can be prepared as described in U.S. Pat. No. 4,026,894. Alternatively, the base can be prepared by reacting 2-chloro-4-amino-6,7-dimethoxyquinazoline and N-(2-tetrahydrofuroyl)piperazine in the presence of a suitable solvent such as Methyl Cellosolve ® (ethylene glycol monomethyl ether) and triethylamine. The reaction mixture is heated to a temperature of between about 115° to about 120° C. for from 7 to 12 hours and then cooled to room temperature. The ether is removed, preferably by vacuum distillation, and the residue is taken up in water, acidified to a pH of between about 2.5 to about 3.0 and mixed for a period of at least 30 minutes. The reaction mixture is then filtered and the pH of the filtrate is adjusted to a pH of about 8.3 to 8.5, preferably with, for example, 28% ammonia water. The basified solution is heated to a temperature of about 60° to 70° C. for about one hour, and thereafter cooled and maintained at a temperature of about 15° to about 20° C. for at least 12 hours. The resulting crystalline product is filtered, washed with cold water and dried to yield the desired base.

Methyl Cellosolve is purchased from Carbide and Carbon Chemicals Co., 30 E. 42nd Street, New York, New York.

The following examples further illustrate the present invention.

EXAMPLE I

Preparation of 1-(4-amino-6,7-dimethoxy-2-quinazolinyl)-4-(2-tetrahydrofuroyl)piperazine Sixty grams (0.25 M) of 2-chloro-4-amino-6,7-dimethoxyquinazoline and 56.8 grams (0.308 M) of N-(2-tetrahydrofuroyl)piperazine were added to a stirred solution of 500 grams of Methyl Cellosolve ® (ethylene glycol monomethyl ether) and 37.9 grams of triethylamine. The reaction mixture was heated to and maintained at a temperature of between 115° to 120° C. for 8 hours, and then allowed to cool to room temperature overnight. The Methyl Cellosolve ® ether was removed by vacuum distillation, the residue was taken up in 1920 ml of 45° C. filtered water, and the temperature of the solution was readjusted to 45° C. The pH was then adjusted to pH 2.5 with concentrated hydrochloric acid and the solution was mixed for 1 hour. The solution was then filtered and the pH adjusted to pH 8.3 with filtered ammonia water (28%). After heating for 1 hour at 65° C., the solution was cooled to 15° C. and held at a temperature of between 15°-20° C. for 16 hours. The resulting crystalline product was filtered, washed with cold water (15° C.) and dried in vacuo at 65° C. to yield 84 grams of anhydrous base.

EXAMPLE 2

Preparation of 1-(4-amino-6,7-dimethoxy-2-quinazolinyl)-4-(2-tetrahydrofuroyl)piperazine hydrochloride dihydrate.

The hydrochloride salt of the dihydrate of the compound of Example 1 was prepared by slurrying 10 grams of the above-prepare 1-(4-amino-6,7-dimethoxy-2-quinazolinyl)-4-(2-tetrahydrofuroyl) piperazine in 150 ml of 190 proof Formula 3A alcohol, heating the slurry to about 35° C., adding 2.5 ml of concentrated (aqueous) hydrochloric acid thereto and heating the mixture to about 70° C. The reaction mixture was carbon treated, the carbon was filtered off and the filtrate was cooled overnight in an icebox. The product was then filtered off and dried at 60° C. to obtain 10 grams of the desired product, m.p. 271°-274° C.

The physical properties of the compound of Formula II and the compound of this invention, referred to hereinafter as the anhydrous and dihydrate, respectively were compared. While the compounds have the same or similar properties in some instances, i.e., optical rotation and elemental analysis there are a number of differences. The following examples compare representative differing properties of the two compounds.

EXAMPLE 3

Differential Thermal Analysis

The anhydrous and dihydrate were subjected to differential thermal analysis with the following results. The anhydrous compound exhibited one melting endotherm at 280° C. No other endotherms or exotherms were noted from ambient temperature to 420° C. The dihydrate exhibited minor endotherms at 147° C. and 170° C. and one major melting endotherm at 278° C.

EXAMPLE 4

Moisture Loss on Drying

A 1.4773 gram sample of the anhydrous compound, dried for 3 hours at 105° C., USP vacuo, showed 1.02% weight loss. A 0.7578 mg. sample of the dihydrate, dried for 3 hours at 100° C., USP vacuo, showed 7.38% weight loss.

EXAMPLE 5

X-Ray Diffraction Patterns

Figure 2:
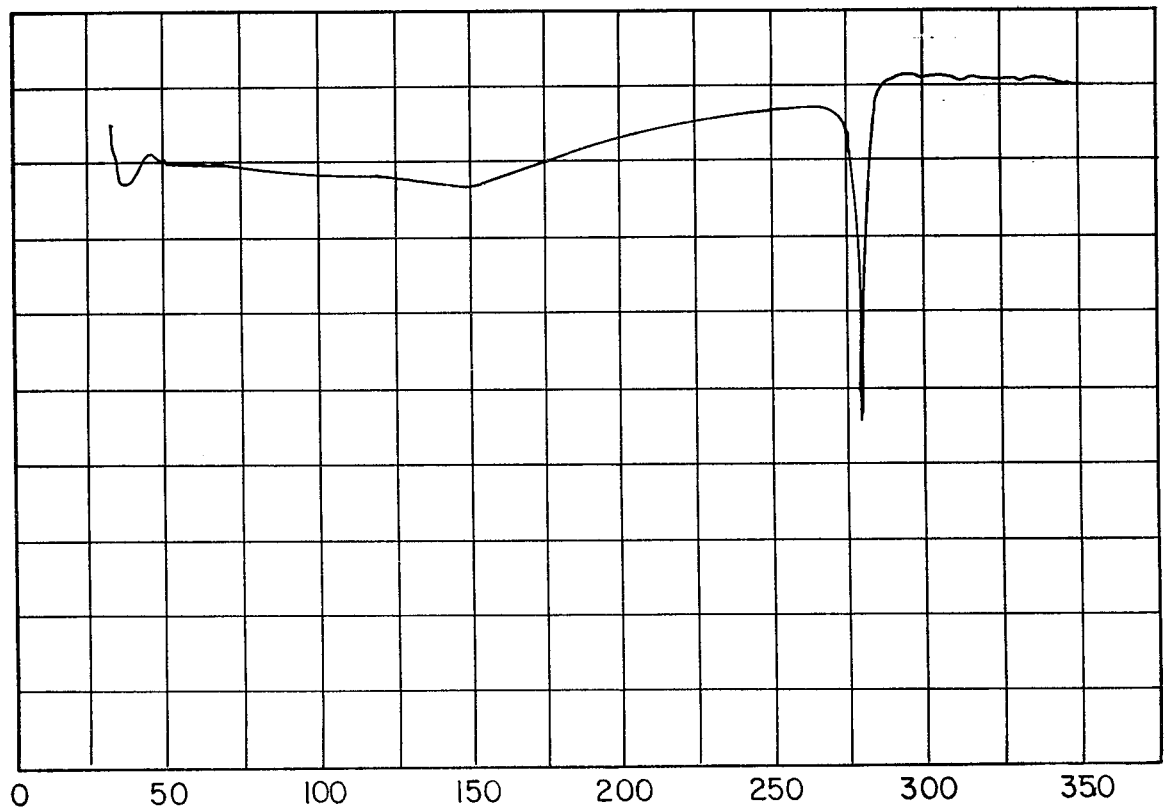

The X-ray diffraction patterns were determined using an Enraf-Nonius Diffractis 601 Generator operating at 38 KV and 18 ma with nickel filtered copper radiation of 1.05418Å. A General Electric Debye-Scherer powder camera of 143.2 mm diameter was used. Both the anhydrous compound and the dihydrate have monoclinic crystal systems, however, their X-ray patterns are different as can be seen from FIGS. 1 and 2.

EXAMPLE 6

Hygroscopicity

The rate of moisture absorption was tested in a vapor-temperature controlled relative humidity chamber (BLue M Electric Company). The results are summarized in Table III.

TABLE I

| Relative Humidity | Time Hrs. | Moisture Absorbtion % Weight Gain Anhydrous | % Moisture Absorbtion Dihydrate |
|---|---|---|---|
| 56.5 | 24 | 0.59 | 0.07 |
| 56.5 | 48 | 0.56 | 0.00 |
| 56.5 | 96 | 0.66 | 0.04 |

EXAMPLE 7

Relative Solubilities

The solubilities of the dihydrate and anhydrous were determined in three different systems: water, pH 1.2 buffer and pH 7.5 buffer. The data are summarized in Table IV.

TABLE II

| Solvent | Anhydrous mg/ml | Dihydrate |
|---|---|---|
| Water | 761.2 mg/ml | 24.2 mg/ml |
| pH 1.2 buffer | 750.0 | 1.99 |
| pH 7.5 buffer | 772 | 55.2 |

The present invention includes within its scope pharmaceutical compositions comprising, as the active ingredient, the compound of Formula III in association with a pharmaceutically acceptable carrier or diluent. The compound of this invention can be administered by oral or parenteral routes of administration and can be formulated in dosage forms appropriate for each route of administration including capsules, tablets, pills, powders and granules. In such solid dosage forms, the active compound is admixed with at least one inert diluent such as sucrose, lactose or starch. The oral dosage forms can also comprise, as is normal practice, addition substances other than inert diluents, e.g., lubricating agents such as magnesium stearate. In the case of capsules, tablets and pills, the dosage forms may also comprise buffering agents. Tablets and pills can additionally be prepared for a sustained release or may be prepared with enteric coatings.

Preparations according to this invention for parenteral administration include sterile aqueous solutions although nonaqueous suspensions or emulsions can be employed. Such dosage forms may also contain adjuvants such as preserving, wetting, emulsifying and dispersing agents. They may be sterilized by, for example, filtration through a bacteria retaining filter, by incorporating sterilizing agents into the compositions, irradiating the compositions, or by heating the compositions.

The dosage of the compound of this invention may be varied: however, it is necessary that the amount of the active ingredient shall be such that a suitable dosage form is obtained. Generally, dosage levels of between 0.01 to 100 mg daily are administered to patients to lower blood pressure and thereafter maintain a normal blood pressure.

The following examples further illustrate the pharmaceutical compositions which are a feature of this invention.

EXAMPLE 8

Tablets weighing 50 mg and having the following compositions are formulated.

| Ingredient | mg |
|---|---|
| 1-(4-amino-6,7-dimethoxy-2-quinazolinyl)-4-(2-tetrahydrofuroyl)piperazine hydrochloride dihydrate | 5.0 |
| starch | 35.0 |
| colloidal silica | 9.5 |
| magnesium stearate | 0.5 |

EXAMPLE 9

Sterile 10 ml ampoules are prepared containing 5 mg per ml of 1-(4-amino-6,7-dimethoxy-2-quinazolinyl)-4-(2-tetrahydrofuroyl)piperazine hydrochloride dihydrate, 0.1% sodium bisulfate, 0.7% sodium chloride and 0.5% chlorobutanol as a preservative.

What is claimed is:

1. The compound 1-(4-amino-6,7-dimethoxy-2-quinazolinyl)-4-(2-tetrahydrofuroyl)piperazine hydrochloride dihydrate.

2. A method of treating hypertension comprising administering a therapeutically effective amount of 1-(4-amino-6,7-dimethoxy-2-quinazolinyl-4-(2-tetrahydrofuroyl) piperazine hydrochloride dihydrate to a patient in need of such treatment.

3. An antihypertensive pharmaceutical composition comprising a therapeutically effective amount of 1-(4-amino-6,7-dimethoxy-2-quinazolinyl-4-(2-tetrahydrofuroyl)piperazine hydrochloride dihydrate and a pharmaceutically acceptable carrier or diluent.

* * * * *

UNITED STATES PATENT AND TRADEMARK OFFICE

CERTIFICATE EXTENDING PATENT TERM
UNDER 35 U.S.C. 156

Patent No.    : 4,251,532

Dated         : February 17, 1981

Inventor(s)   : Robert Roteman

Patent Owner  : Abbott Laboratories

This is to certify that there has been presented to the

COMMISSIONER OF PATENTS AND TRADEMARKS an application under 35 U.S.C. 156 for an extension of the patent term. Since it appears that the requirements of law have been met, this certificate extends the term of the patent for the period of

2 YEARS with all rights pertaining thereto as provided by 35 USC 156(b).

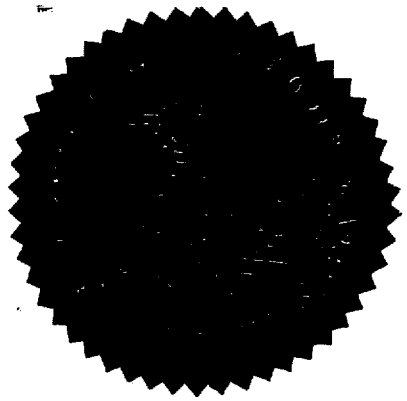

I have caused the seal of the Patent and Trademark Office to be affixed this Sixteenth day of August 1988.

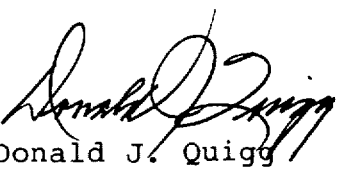

Donald J. Quigg

Assistant Secretary and Commissioner of Patents and Trademarks